May 23, 1972 J. R. BEARSS Plant Pat. 3,187
ILEX PLANT
Filed Sept. 9, 1970
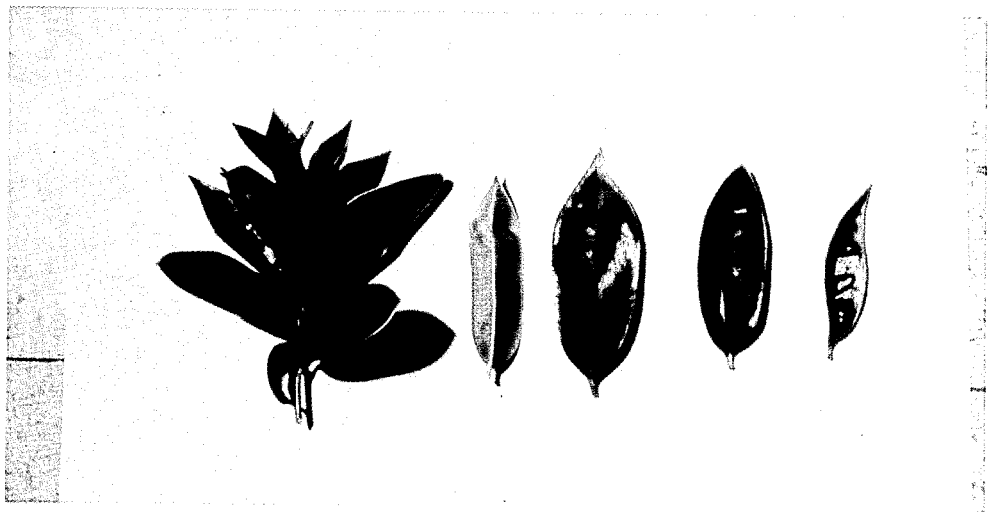
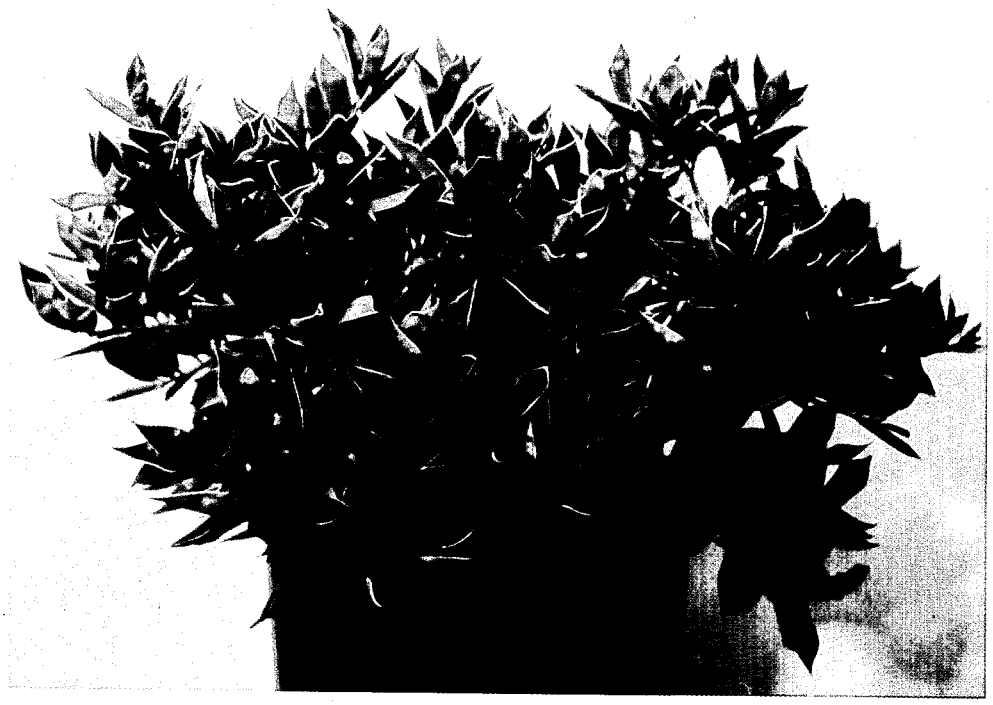
Inventor
John R. Bearss
Burns, Doane, Swecker & Mathis
Attorneys United States Patent Office Plant Pat. 3,187
Patented May 23, 1972

3,187

ILEX PLANT

John R. Bearss, Cairo, Ga., assignor to Wight Nurseries, Inc., Cairo, Ga.

Filed Sept. 9, 1970, Ser. No. 70,942
Int. Cl. A01h 5/00
U.S. Cl. Plt.—65 1 Claim

ABSTRACT OF THE DISCLOSURE

A new and distinct variety of Ilex plant which was originated as a bud mutation of *Ilex cornuta Rotunda.*

SUMMARY OF DISCLOSURE

The present invention relates to a new and distinct variety of Ilex plant which was originated as a bud mutation of *Ilex cornuta Rotunda.*

The plant has characteristics which distinguish it from all other *Ilex cornuta* varieties and which characterizes it as a new and distinct variety in the following ways:

(1) Upper surface of most leaves prominently concave. *Cornuta Rotunda* leaves appear to be more or less prominently revolute, each side of upper surface convex.

(2) Margin of almost all leaves entire with a single rigid terminal prickle.

(3) Edge of leaves very prominent because of obvious difference in coloring—paler green at the edge.

(4) Leaves of lower branches tending to twist on their petioles so as to be suberect and secund on these branches.

(5) Slower growing than most Ilex varieties, this variety has more spread than height and the parent plant has attained a height of 24 inches and spread of about 36 inches in 5 years.

Asexual reproduction of the new variety was made by cuttings as performed at Cairo, Ga., showing that the foregoing characteristics and distinctions come true to form and are established and transmitted through succeeding propagations.

The accompanying drawings show a typical specimen plant illustrating its general habit of growth and also show typical specimens of wood and foliage of my new variety, both of which are depicted in color as nearly true as it is reasonably possible to make the same in a color illustration of this character.

The following is a detailed description of my new variety, with color terminology in accordance with A Dictionary of Color, by A. Maerz and M. Rea Paul, published by McGraw Hill Book Company in 1930:

Form: Dwarfish, copiously branched from most upper nodes, the internodes short, the leaves ascending—spreading.

Growth habit: Low; stiffly erect and ascending; the branches, compact—spreading, the crown broader than high; slow growing, would attain a height of 3 feet in 8 years.

Blooming season: Not known; no flowers observed.

Foliage: Leaves alternate, occasionally opposite or almost opposite, spirally arranged and evenly disposed on erect shoots, ascending on twisted petioles, on lateral branches; internodes short (from ⅛ to ¼″ on most new growth).

*Size.*—Petioles ¼ to ⅛″ long; blades on oldest shoots 1 to 2 inches long, on newest shoots up to 3 inches long, averaging between 1½ and 2 inches long, and ¾ to 1 inch broad.

*Quantity.*—Abundant; older leaves persisting several years; nodes short, the lowest often branching, hence the shrub very compact.

*Color.*—Juvenile foliage: Maroon as in *Ilex cornuta Rotunda.* Fully expanded. New foliage: upper side, "Brunswick Green," lustrous (plate 23, C–12)—lower side, "Sea Green" (plate 19, K–6). Old foliage: upper side, darker green, lustrous (plate 23, L–12); lower side, "Sea Green" (plate 19, K–6). Edge of leaf very prominent, being "Chrysolite Green" (plate 19, K–3) and conspicuously different colored from top of leaf.

*Shape.*—Leaves on oldest shoot growth ovate with apices either acute or narrowly rounded and without a prickle or acuminate, with a rigid terminal prickle: leaves on newest shoots tending to be longer, oblong and acuminate, almost all with a rigid terminal prickle. Bases of all leaves rounded to broadly cureate.

*Texture.*—Coriaceous; surfaces all smooth; main lateral veins somewhat impressed above and slightly paler than rest of surface, these same veins indistinct or slightly raised below—upper surface—relatively dark and semi-glossy, concave—lower surface—pale, convex.

*Margin.*—Entire (very occasionally with lateral prickle) with a distinct, thick pale edge and a single rigid pale, terminal prickle.

Disease and insect resistance: Comparable to *Ilex cornuta Rotunda.*

Flower: Neither flowers nor fruit have as yet developed in this, a bud mutation.

I claim:

1. A new and distinct variety of Ilex plant of the *Ilex cornuta Rotunda* type, substantially as herein shown and described, characterized particularly as to novelty by the upper surface of most leaves being prominently concave; the margin of almost all leaves being entire with a single rigid terminal prickle; with the edges of the leaves very prominent and of paler green than the remainder of the leaves; the leaves on the lower branches tending to twist on their petioles; and the plant being of low growth and spreading and broader in width than height.

No references cited.

ROBERT E. BAGWILL, Primary Examiner